United States Patent [19]
Muñoz Quintana

[11] Patent Number: 5,788,931
[45] Date of Patent: Aug. 4, 1998

[54] AIR FRESHNER FOR MOTOR VEHICLES

[76] Inventor: Jose Muñoz Quintana, Murillo, 43, 3º3ª, Cornella de Llobregat (Barcelona), Spain, 08940

[21] Appl. No.: 662,067

[22] Filed: Jun. 12, 1996

[30] Foreign Application Priority Data

Mar. 21, 1996 [ES] Spain ..................... 9600819

[51] Int. Cl.$^6$ ..................... A61L 9/03
[52] U.S. Cl. ............... 422/125; 422/5; 392/390; 239/35; 219/202
[58] Field of Search ............... 219/202, 505; 392/390, 395, 403; 422/125, 4, 5; 239/35, 60

[56] References Cited

U.S. PATENT DOCUMENTS

| 5,126,078 | 6/1992 | Steiner et al. | 261/26 |
| 5,170,067 | 12/1992 | Baum et al. | 307/10.1 |
| 5,373,581 | 12/1994 | Smith | 392/390 |

FOREIGN PATENT DOCUMENTS 2062199   5/1981   United Kingdom .

*Primary Examiner*—Timothy McMahon
*Assistant Examiner*—Alex Noguerola
*Attorney, Agent, or Firm*—Richard M. Goldberg

[57] ABSTRACT

An air freshener for motor vehicles, of a type inserted inside an electrical lighter of a vehicle and using current from the electrical lighter, includes a casing for holding an air freshening material of a pastille or gel form therein, the casing having a cover; a main resistor surrounded by the casing and which is electrically activated by the current to generate heat; a printed circuit board with resistors of lower voltage rating than the main resistor and connected to the main resistor; holes in the cover for entry of air; interior projections in the casing for holding the air freshening material; a buzzer placed inside the casing, activated by the current and triggered by a time mechanism corresponding to usage time; two electrical poles for receiving current from the electrical lighter; at least one wire for connecting the two electrical poles with the printed circuit board and/or main resistor; and a light which is illuminated by the current during activation of the main resistor.

10 Claims, 2 Drawing Sheets

AIR FRESHNER FOR MOTOR VEHICLES

BACKGROUND OF THE INVENTION

The invention refers to an improved air freshener for motor vehicles, in order to ensure suitably scented air inside the vehicle. It may also bear insecticidal substances or other substances which improve the safety and hygiene characteristics in vehicles which usually circulate with the windows closed and consequently generate bad odors, smoke or other similar problems inside the car.

SUMMARY OF THE INVENTION

To this end, a very simple device has been designed, which uses the electrical current of the vehicle's cigarette lighter to vaporise a substance that will release a pleasant scent inside the vehicle, at the same time as eliminating the bad odors derived from tobacco or continued closure of the vehicle. This it will do with considerable efficiency, since it does not release the substance by natural means, but forceably by means of the temperature.

The claimed device comes inserted inside a casing which is of a size suitable for placing inside the vehicle's electric lighter. This means that it does not take up any space interior, and that it can use the electrical current available at the said point of the vehicle.

In order to achieve a perfect connection between the electric lighter and the said device, the latter disposes of two poles of opposite charges, connected to each other by electrical wiring or simple contact of the different elements located between the two. All this is arranged in such a way that the poles make contact with the corresponding elements of the lighter, while it is anticipated that an LED will light up while the device is operating.

Similarly, the air freshening, insecticidal substance will be found inside the said casing, duly protected. It may be solid, in the form of pastilles of different quantities, or in the form of a gel.

Operation of this small device is very simple; it will be sufficient to move it slightly backward or forward in the vehicle's lighter in order to connect the opposite poles and the electrical circuit of the vehicle. This will trigger the interior circuit of the said mechanism. This is visually verifiable from the outside, such that the LED mentioned above will light up to confirm operation.

For the purposes of the present improved air freshener, it is essential that there be a resistor connected to a printed circuit board which will have several small resistors. These will serve to protect the main resistor, ensuring that any small changes in voltage will not have any negative effects on the life of the main resistor.

Likewise, it is essential that when the air freshener is in a pastille in the solid state, different quantities of pastilles may be used, and that suitable protections be provided to hold them.

Finally, an option will be available to place an electric buzzer with a timing device inside the said air freshener, so that the user will know when the air freshener has come to the end of its useful life and the substance contained inside it must be replaced. This is bound to represent a significant advantage for ensuring correct use of the mechanism in question.

BRIEF DESCRIPTION OF THE DRAWINGS

In order to facilitate comprehension of the explanation, a page of drawings is enclosed with the present statement, by way of illustration and not being in any way restrictive, representing an example of an improved air freshener for motor vehicles, according to the principles set forth in the claims.

In the drawings.

Finally.

DETAILED DESCRIPTION

Figure 1:
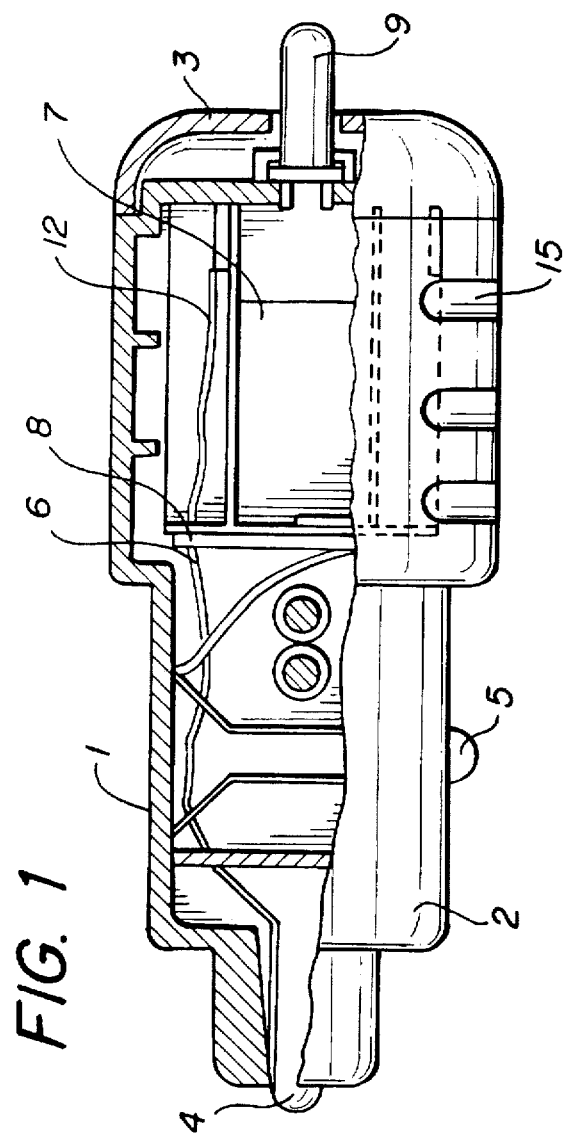
FIG. 1 shows a partially sectioned elevation view of the improved air freshener for motor vehicles with a pastille.
Figure 2:
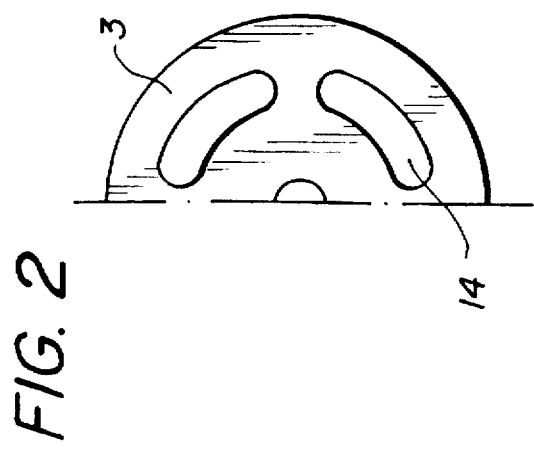
FIG. 2 shows a cross section of the same from the cover.
Figure 3:
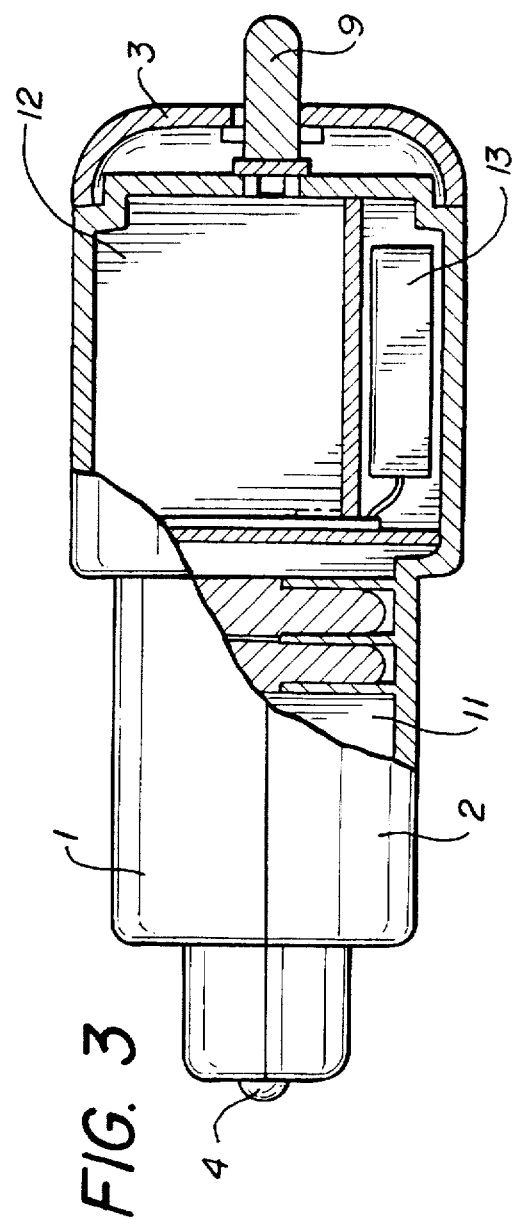
FIG. 3 shows a partially sectioned top view of the air freshener in question, in the case of three pastilles.
Figure 4:
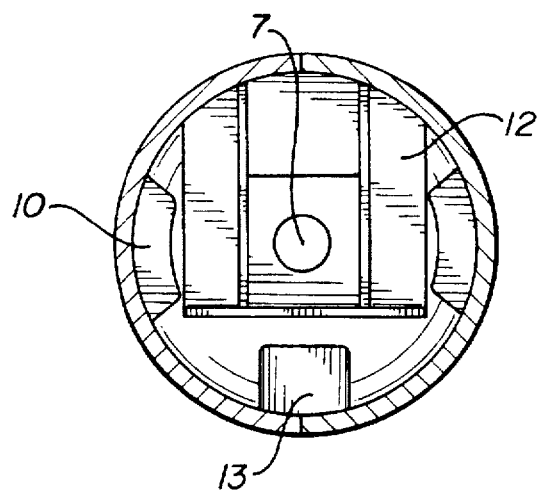
FIG. 4 shows a cross section of the same, crossing the area in which the air freshening product is located.
Figure 5:
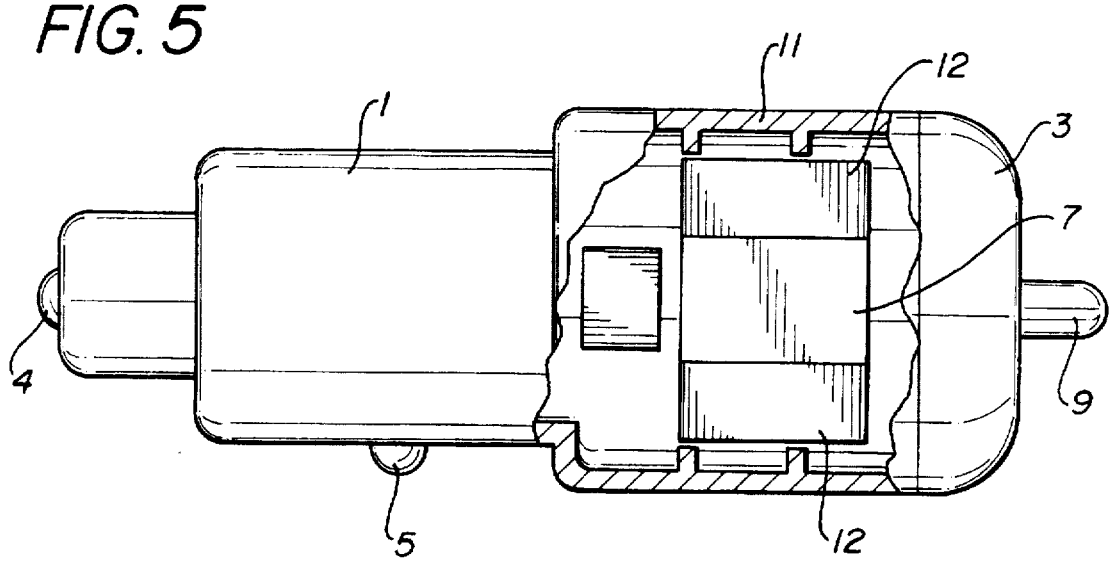
FIG. 5 shows another example of production of the said air freshener, in which the device contains two pastilles. The cross section is shown in FIG. 6.
Figure 6:
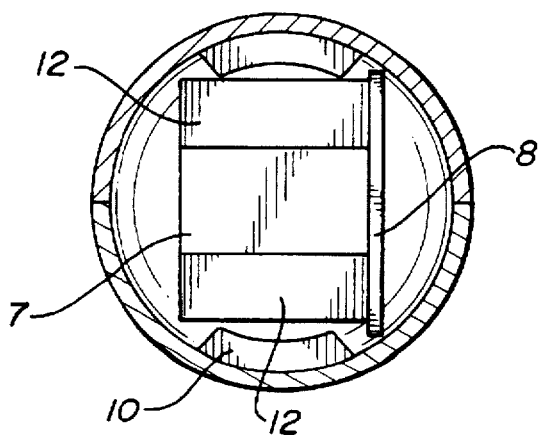

As shown in the drawings, the improved air freshener for motor vehicles comprises an outer casing which, in the case of exchangeable pastilles, is composed of an upper part -1-, a lower part -2- and a closing cover -3-, which together enclose the different elements of the interior.

The internal elements are especially constituted by the two electrical poles, one positive -4- and the other negative -5-. They are connected to each other and to the interior electrical elements by a wire -6- in the case illustrated, while the electrical element itself comprises a resistor -7- and a printed circuit board -8-. The latter is provided, inter alia, with some small protective resistors. An LED -9- is also connected to the said circuit.

Several projections -10- -11- are provided in the interior wall of the device, with the purpose of holding different pastilles -12- containing the product. These will be placed in different positions, depending on the number contained in the device. The device may be either disposable or reloadable, and if three pastilles are to be placed inside it, a plate or tray will be provided to protect the central resistor.

An optional, but equally important feature, is the buzzer -13- to be placed inside the device. Its action is controlled by a timing circuit which contains data on the duration in hours of an air freshening pastille. When the said number of hours is reached, the buzzer is triggered and warns the driver of this situation.

In order to facilitate the necessary movement of air inside the air freshener, ensuring that the vapours of the air freshening substance contained are released to the outside, some holes -14- have been provided in the cover -3-, and others -15- in the side casing.

The operation of the device is very simple. Once the air freshener has been inserted in the vehicle's lighter in such a way that terminals -4- and -5- are in contact with the corresponding lighter terminals, an electric current is produced inside the air freshener, activating the resistor. This in turn generates a certain quantity of heat facilitating the release of an air freshening substance located inside the device. The said substance is released to the outside via the holes -14- provided for this purpose, helped by the flow of air created by the existence of inlets -14- in the cover. In this way, the scent fills the inside of the vehicle and improves the characteristics of the air in the same.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention as defined by the appended claims.

I claim:

1. An air freshener for motor vehicles, to be inserted inside an electrical lighter of a vehicle and using current from the electrical lighter, comprising:

a casing holding an air freshening material therein, said casing having a cover;

a main resistor surrounded by said casing and which is electrically activated by said current to generate heat for heating the air freshening material;

a printed circuit board with resistors of lower voltage rating than said main resistor and connected to the main resistor in such a manner so as to protect the main resistor so that changes in voltage will not adversely effect the life of said main resistor;

holes in the cover for entry of air;

interior projections in the casing for holding the air freshening material; and means provided in the casing for providing an indication that new air freshening material must be provided in the casing.

2. An air freshener for motor vehicles according to claim 1, wherein the means for providing an indication includes a buzzer placed inside said casing, activated by said current and triggered by a time mechanism corresponding to usage time.

3. An air freshener for motor vehicles according to claim 1, further comprising:

two electrical poles for receiving current from the electrical lighter; and at least one wire for connecting said two electrical poles with at least one of the printed circuit board and main resistor.

4. An air freshener for motor vehicles according to claim 1, wherein said air freshener is disposable after exhaustion of said air freshening material.

5. An air freshener for motor vehicles according to claim 1, wherein said air freshening material is reloadable after exhaustion of said air freshening material.

6. An air freshener for motor vehicles according to claim 1, wherein said air freshening material is in the form of a number of pastilles.

7. An air freshener for motor vehicles according to claim 6, wherein the position of the interior projections will change in accordance with the number of pastilles held inside the casing.

8. An air freshener for motor vehicles according to claim 1, wherein said air freshening material is in a gel form.

9. An air freshener for motor vehicles according to claim 1, further comprising:

two electrical poles for receiving current from the electrical lighter, said two electrical poles being in contact with at least one of the printed circuit board and main resistor.

10. An air freshener for motor vehicles according to claim 1, further comprising a light which is illuminated by said current during activation of said main resistor.

* * * * *

UNITED STATES PATENT AND TRADEMARK OFFICE
CERTIFICATE OF CORRECTION

PATENT NO. : 5,788,931
DATED : August 4, 1998
INVENTOR(S) : Jose MUNOZ QUINTANA

It is certified that error appears in the above-indentified patent and that said Letters Patent is hereby corrected as shown below:

On the title page, and column 1:

"FRESHNER" to -- FRESHENER --.

Signed and Sealed this

Sixth Day of October, 1998

Attest:

BRUCE LEHMAN

Attesting Officer

Commissioner of Patents and Trademarks